United States Patent [19]

Ford et al.

[11] Patent Number: 4,766,247

[45] Date of Patent: Aug. 23, 1988

[54] COLOR REDUCTION OF POLYAMINES BY MILD CATALYTIC HYDROGENATION

[75] Inventors: Michael E. Ford, Center Valley; Thomas A. Johnson, Orefield; Gamini A. Vedage, Bethlehem, all of Pa.

[73] Assignee: Air Products and Chemicals, Inc., Allentown, Pa.

[21] Appl. No.: 912,882

[22] Filed: Sep. 26, 1986

[51] Int. Cl.$^4$ .............................................. C07C 85/26
[52] U.S. Cl. ...................................... 564/498; 564/2; 564/479
[58] Field of Search ........................... 564/498, 479, 2

[56] References Cited

U.S. PATENT DOCUMENTS

| | | | |
|---|---|---|---|
| 3,723,529 | 3/1973 | Pitts et al. | 564/498 |
| 4,347,381 | 8/1982 | Tuvell | 564/2 |
| 4,463,193 | 7/1984 | Johnson et al. | 564/479 |
| 4,487,987 | 12/1984 | Paslean et al. | 568/756 |
| 4,503,253 | 3/1985 | Ford et al. | 564/479 |
| 4,567,303 | 1/1986 | Boettger et al. | 564/475 |
| 4,570,019 | 2/1986 | Gibson et al. | 564/498 |

FOREIGN PATENT DOCUMENTS 44-02209 1/1969 Japan .
44-04768 2/1969 Japan .
45-33163 10/1970 Japan .
48-52708 7/1973 Japan .

OTHER PUBLICATIONS

U.S. Ser. No. 674,611 "Polyalkylene Polyamines Via Vapor Phase Reaction" Ford et al.

*Primary Examiner*—Glennon H. Hollrah
*Assistant Examiner*—John A. Sopp
*Attorney, Agent, or Firm*—Willard Jones, II; James C. Simmons; William F. Marsh

[57] ABSTRACT

The present invention relates to a process for the reduction of the color of polyamines by reacting at elevated temperature, i.e. 50° to 175° C., and pressure, i.e. 50 to 1500 psig, such colored polyamines, e.g. triethylenetetramine or tetraethylenepentamine, in the presence of a hydrogenation catalyst, e.g. Raney nickel or palladium on carbon, and a hydrogen atmosphere for a period of time sufficient to effectuate the desired reduction in color. In the process of the present invention, the polyamines can either be distilled into a narrow product composition and then hydrogenated or a crude polyamine product can be hydrogenated and then distilled to produce the desired product composition.

10 Claims, No Drawings

COLOR REDUCTION OF POLYAMINES BY MILD CATALYTIC HYDROGENATION

TECHNICAL FIELD

The present invention relates to a process for the reduction of the color of mixed polyamine products by mild hydrogenation.

BACKGROUND OF THE INVENTION

Several processes have been proposed or used commercially for the removal of color bodies from mixed polyamine products; these processes encompass both physical and chemical methods.

U.S. Pat. No. 3,723,529 discloses a process for the removal of color bodies which comprises treatment of the polyamine with activated carbon at elevated temperatures, 200°–280° C., and subsequent removal, preferably by filtration, of the activated carbon. The resultant polyamine mixture would then be distilled into the desired cuts.

U.S. Pat. No. 4,347,381 discloses a process for the removal or elimination of a pink color content from long chain alkyl amines by treating such products with a trace amount of a bleaching agent. Optionally, the bleaching agent treated amine product can then be heated for a short period of time to improve effectiveness of the bleaching.

U.S. Pat. No. 4,487,987 discloses a method of eliminating color-causing impurities in mixtures of aminoethylpiperazine, polyoxypropylenediamines and alkylphenols by treatment with N,N-diethylhydroxylamine. Quantities on the order of 20 to 500 ppm are effective and the decolorization reaction is conducted at a temperature in the range of about 25° to 50° C.

U.S. Pat. No. 4,567,303 discloses a process for the preparation of colorless alkanolamines in which the process is carried out in a reactor system which is constructed of substantially nickel-free steel. The patent teaches that it is the presence of nickel in the steel walls of the reactor system which causes the color bodies to form, therefore elimination of the nickel in the reactor system produces colorless alkanolamines.

U.S. Pat. No. 4,570,019 discloses a process which can be run continuously for producing polyethylene polyamines having improved color characteristics. The process encompasses treating the discolored polyethylene polyamines with polyethylene polyamine hydrochloride in the presence of water at elevated temperatures for the time necessary to reduce the color of the polyethylene polyamines and then flashing the mixture to evaporate the decolorized polyethylene polyamines from the treating mixture.

Japanese Patent Application No. 39-27478 discloses a process for decolorizing ethylene amines characterized in that at least one metal from among zinc, aluminum, and tin and at least one alkali selected from sodium hydroxide and potassium hydroxide are added to the discolored amines and heated.

Japanese Patent Application No. 40-1330 discloses a process for decolorizing polyethylene polyamines by bringing the discolored polyamine into intimate contact with zinc and water at room temperature to about 150° C.

Japanese Patent Application No. 43-53148 discloses a process for decolorizing ethylene amines by adding zinc to the colored ethylene amine followed by heating.

BRIEF SUMMARY OF THE INVENTION

The present invention relates to a process for the reduction of the color of polyamines by contacting at elevated temperature, i.e. 50° to 175° C., and pressure, i.e. 50 to 1500 psig, such colored polyamines, e.g. triethylenetetramine or tetraethylenepentamine, with a catalytically effective amount of a hydrogenation catalyst, e.g. Raney nickel or palladium on carbon, in the presence of a hydrogen containing atmosphere for a period of time sufficient to effectuate the desired reduction in color. In the process of the present invention, the polyamines can either be distilled into a narrow product composition and then hydrogenated or a crude polyamine product can be hydrogenated and then distilled to produce the desired product composition. As an optional step for the situation where narrow product compositions are separately hydrogenated, the hydrogenated polyamine product can be distilled to further reduce the color by removing any chromophores which may have polymerized during the hydrogenation process.

DETAILED DESCRIPTION OF THE INVENTION

Polyethylene amines such as triethylenetetramine (TETA) or tetraethylenepentamine (TEPA) which have been produced by reacting an alkanolamine compound, an alkyleneamine and optionally either ammonia or a primary or secondary amine in the presence of a catalytically effective amount of a phosphorous containing catalyst, e.g. phosphoric acid on silica-alumina or Group IIIB metal acid phosphate, at a temperature from about 175° to 400° C. under a pressure sufficient to maintain a substantial amount of ammonia or amine in the reaction zone and particularly under vapor phase conditions, rapidly develop a tan to brown color, i.e. 7–8 on the Gardener scale, ASTM Method D-1544. This color limits the range of application of TETA and TEPA.

To lower the color of polyethylene polyamines or other polyalkylene polyamines, we have found that if the product polyamines are subjected to a mild hydrogenation process then the color problem is lessened. Basically, product polyamines from any polyamine preparation process, such as are disclosed in U.S. Pat. Nos. 4,463,193 and 4,503,253 and U.S. patent application Ser. No. 674,611 and which are incorporated herein by reference, are reacted with a hydrogen atmosphere in the presence of a hydrogenation catalyst at elevated temperature and pressure. It is believed that during the process chromophores, i.e. color bodies, are reduced or eliminated; the exact mechanism of the process is unknown.

As stated above, the process basically comprises contacting a polyamine product with a catalytically effective amount of a hydrogenation catalyst in the presence of a hydrogen containing atmosphere at elevated temperature and pressure. For the process, the polyamine product can be any polyalkylene polyamine. This polyamine product produced by any of the applicable preparation processes can either be treated for color reduction as a crude product, i.e. as produced from the applicable preparation process, or be distilled into selected cuts and then treated.

Generally, any catalytic metal which has known hydrogenation properties would be applicable for use in the present invention. Among these metals are nickel, palladium, ruthenium, molybdenum, tungsten, cobalt and chromium. These catalytic metals can be supported on standard base materials, e.g. carbon, silica, alumina, aluminosilicates, and used as the catalyst for the process or they can be used in an unsupported mode. Catalyst loadings for the process are dependent on the type of polyamine product and the particular hydrogenation catalyst being used.

The process of the present invention can either be performed in a batch or continuous mode of operation utilizing either a fixed bed or slurry reactor type. Operating ranges for such would be as follows:

Temperature: °C. 50 to 175
Hydrogen Partial Pressure: psig 50 to 1500
Batch Times: hr 0.1 to 4
Space Velocity: v/hr/v 0.01 to 10

To demonstrate the efficacy of the present invention, several polyethylene polyamine products were reacted with a hydrogen atmosphere in the presence of a metal hydrogenation catalyst at varying pressures, temperatures and residence times and are offered as the following examples.

EXAMPLES 1-8

Color Reduction of TETA and TEPA Polyamines

Preparation of TETA and TEPA: A polyethylene polyamine product was produced using the process of U.S. Pat. No. 4,462,193. Basically, a mixture of monoethanolamine (MEA), ethylenediamine (EDA) and ammonia ($NH_3$) (mole ratio EDA:MEA:$NH_3$ was 2:1:8) was passed over a lanthanum acid phosphate catalyst at a gas hourly space velocity of 2500 vol/hr/vol based on all components, at 250 psig and 250° C. The resultant liquid product was distilled to remove two cuts: a TETA cut (145°–155° C. at 10 mm Hg) and a TEPA cut (190°–205° C. at 10 mm Hg). The TETA and TEPA cuts obtained are not pure triethylenetetramine and tetraethylenepentamine respectively but a mixture of isomers of noncyclic and cyclic polyamines having the same general boiling range. Analysis of the TETA and TEPA cuts are listed in Table I.

TABLE I

| TETA AND TEPA FEED COMPOSITIONS | | |
|---|---|---|
| Component | TETA wt % | TEPA wt % |
| Diethylenetriamine (DETA) | 0.5 | 0.6 |
| Aminoethylethanolamine (AEEA) | 0.19 | 0.11 |
| Aminoethylpiperazine (AEP) | 0.12 | 0.25 |
| Tris(aminoethyl)amine (TAEA) | 11.79 | 1.37 |
| Triethylenetetramine (TETA) | 58.94 | 12.95 |
| Bis(aminoethyl)piperazine (BAEP) | 25.86 | 3.63 |
| Piperazinoethylethylenediamine (PEEDA) | 0.23 | 3.62 |
| Aminoethyltriethylenetetraamine (AETETA) | 0.00 | 16.2 |
| Tetraethylenepentamine (TEPA) | 0.00 | 21.71 |
| Aminoethylbis(aminoethyl)piperazine (AEBAEP) | 0.00 | 20.43 |
| Aminoethyl(piperazinoethyl)ethylenediamine (AEPEEDA) | 0.00 | 4.82 |
| Total Unknowns | 2.37 | 14.29 |
| Total Noncyclic Polyamines (TNC) | 73.0 | 52.8 |

Hydrogenation Decolorization: The TETA or TEPA cuts (75 g), which are a mixture of isomers, were charged to a 300 ml stainless steel autoclave. The hydrogenation catalyst (see Table II) is added, and the autoclave is thoroughly flushed with hydrogen to remove adventitious air. After pressurization with hydrogen, the reaction mixture is heated with stirring (see Table II for pressure, temperature and batch time). At the completion of the reaction cycle, the hydrogenated polyamines were removed from the reactor and filtered to remove any retained catalyst. Feed and product color numbers are listed in Table II. The color numbers listed in these examples and elsewhere in this disclosure are measured on the Gardner scale. The Gardner number is determined according to ASTM procedure D-1544.

TABLE II

| Catalyst, Operating Conditions, Feed Color and Product Color | | | | | | |
|---|---|---|---|---|---|---|
| | | Catalyst | Time | Temperature | $H_2$ Pressure | Color | |
| Example | Feed | (wt %) | (hr) | (° C.) | (psig) | Feed | Product |
| 1 | TETA | Raney Ni (5.0) | 1 | 100 | 150 | 7+ | 3+ |
| 2 | TETA | Raney Ni (5.0) | 2 | 100 | 150 | 7+ | 1 |
| 3 | TETA | Raney Ni (5.0) | 4 | 100 | 150 | 7+ | 0 |
| 4 | TETA | Raney Ni (5.0) | 1 | 100 | 300 | 7+ | 0 |
| 5 | TETA | 5% Pd/C (0.5) | 1 | 100 | 150 | 7+ | 0 |
| 6 | TETA | 5% Pd/C (0.5) | 1 | 100 | 300 | 7+ | 0 |
| 7 | TEPA | 0.5% Pd/C (0.4) | 24 | 150 | 1000 | 10 | 7 |
| 8 | TEPA | 0.5% Ru/C (0.4) | 21 | 150 | 1000 | 10 | 5 |

The product composition was then determined by gas liquid chromatography; product analyses are listed in Table III.

TABLE III

| EXAMPLE 1-8 PRODUCT COMPOSITIONS | | | | | | | | | |
|---|---|---|---|---|---|---|---|---|---|
| Component | TETA wt % | EX 1 wt % | EX 2 wt % | EX 3 wt % | EX 4 wt % | EX 5 wt % | EX 6 wt % | TEPA wt % | EX 7 wt % | EX 8 wt % |
| Diethylenetriamine (DETA) | 0.5 | 0.45 | 0.45 | 0.53 | 0.44 | 0.39 | 0.41 | 0.60 | 0.57 | 1.11 |
| Aminoethylethanolamine (AEEA) | 0.19 | 0.22 | 0.22 | 0.16 | 0.17 | 0.24 | 0.23 | 0.11 | 0.08 | 0.07 |
| Aminoethylpiperazine (AEP) | 0.12 | 0.27 | 0.71 | 1.16 | 0.51 | 0.24 | 0.26 | 0.25 | 0.42 | 0.62 |
| Tris(aminoethyl)amine (TAEA) | 11.79 | 12.37 | 11.97 | 11.61 | 12.24 | 12.32 | 12.33 | 1.37 | 0.81 | 1.07 |
| Triethylenetetramine (TETA) | 58.94 | 57.43 | 57.48 | 57.23 | 57.87 | 56.92 | 56.97 | 12.95 | 7.54 | 8.27 |

TABLE III-continued

| Component | TETA wt % | EX 1 wt % | EX 2 wt % | EX 3 wt % | EX 4 wt % | EX 5 wt % | EX 6 wt % | TEPA wt % | EX 7 wt % | EX 8 wt % |
|---|---|---|---|---|---|---|---|---|---|---|
| EXAMPLE 1-8 PRODUCT COMPOSITIONS | | | | | | | | | | |
| Bis(aminoethyl)piperazine (BAEP) | 25.86 | 26.52 | 26.87 | 27.14 | 26.91 | 27.99 | 27.67 | 3.63 | 2.35 | 2.78 |
| Piperazinoethylethylenediamine (PEEDA) | 0.23 | 0.69 | 0.72 | 0.79 | 0.67 | 0.61 | 0.54 | 3.62 | 2.98 | 3.97 |
| Aminoethyltriethylenetetraamine (AETETA) | 0.00 | 0.00 | 0.00 | 0.00 | 0.00 | 0.00 | 0.00 | 16.20 | 17.45 | 15.25 |
| Tetraethylenepentamine (TEPA) | 0.00 | 0.00 | 0.00 | 0.00 | 0.00 | 0.00 | 0.00 | 21.71 | 20.38 | 19.77 |
| Aminoethylbis(aminoethyl)piperazine (AEBAEP) | 0.00 | 0.00 | 0.00 | 0.00 | 0.00 | 0.00 | 0.00 | 20.43 | 24.50 | 24.37 |
| Aminoethyl(piperazinoethyl)ethylenediamine (AEPEEDA) | 0.00 | 0.00 | 0.00 | 0.00 | 0.00 | 0.00 | 0.00 | 4.82 | 6.02 | 5.56 |
| Total Unknowns | 2.37 | 2.04 | 1.58 | 1.39 | 1.20 | 1.29 | 1.58 | 14.29 | 16.87 | 17.16 |
| Total Noncyclic Polyamines (TNC) | 73.0 | 72.0 | 71.6 | 71.1 | 71.8 | 70.8 | 71.1 | 52.8 | 46.8 | 45.5 |

As can be seen from the data listed for Examples 1-8, mild catalytic hydrogenation of polyamines, especially TETA, results in a generally decolorized polyamine product. Although the exact mechanism of this color reduction is unknown, it most likely relies on the reduction of chromophores or color bodies. Characterization of this mild hydrogenation process as a catalytic reduction is supported by the dependence of decolorization with the Raney nickel catalyst on reaction time, Examples 1 and 2, and hydrogen partial pressure, Examples 1 and 4.

Essentially colorless TETA is obtained directly by the process of the present invention for hydrogenation with a fresh catalyst. Further processing steps, e.g. distillation, are not required to obtain a decolorized product. However, as will be shown later distillation may be required to achieve essentially colorless color levels as the catalyst ages. The isomeric composition of the TETA decolorized by the process of the present invention is not altered to any degree.

More severe conditions are necessary to decolorize TEPA by the process of the present invention and as can be seen from the data for Examples 7 and 8, only partial removal of the color was achieved even at high hydrogen partial pressures, e.g. 1000 psig. As will be shown later, further processing, such as distillation, may further reduce the color of the product. As with the TETA hydrogenation, the TEPA hydrogenation produced little to no change in the isomeric composition of the product.

To determine the color stability of the decolorized polyamine products from Examples 1-8, portions of the product were stored in clear bottles without an inert atmosphere blanket on the laboratory bench and were subjected to changes in the ambient conditions of the laboratory and to light. The effect of the change in the product color of the polyamine products is shown in Table IV.

TABLE IV

| | Stability of Decolorized Products | | | | |
|---|---|---|---|---|---|
| Example | Color (Days) | | | | |
| 1 | 3+ (0.5) | 3+ (7.0) | 3+ (37.0) | 3+ (56.0) | — |
| 2 | 1 (0.5) | 1 (8.0) | 1 (38.0) | 1 (57.0) | — |
| 3 | 0 (0.5) | 0 (5.0) | 0 (35.0) | 0 (54.0) | 0 (167) |
| 4 | 0 (0.5) | 0 (1.0) | 0 (31.0) | 0 (50.0) | 0 (163) |
| 5 | 0 (0.5) | 0 (1.0) | 0 (24.0) | 0 (48.0) | 0 (161) |
| 6 | 0 (0.5) | 0 (14.0) | 0 (23.0) | 0 (42.0) | 0 (155) |
| 7 | 7 (0.5) | 7 (6.0) | 7 (33.0) | 8 (62.0) | — |
| 8 | 5 (0.5) | 5 (11.0) | 5 (30.0) | 5+ (57.0) | — |

As can be seen from Table IV, over the storage times shown no appreciable change in the product color occurred.

EXAMPLES 9-13

Effects of Catalyst Aging

To determine catalyst life for the process and the effect of catalyst aging on the process, a TETA product was produced and split into five portions. Each of these portions were then hydrogenated in a series of experiments utilizing the same catalyst.

Preparation of TETA feed: A polyethylene polyamine product was produced using the process of U.S. Pat. No. 4,503,253. A mixture of monoethanolamine (MEA), ethylenediamine (EDA) and ammonia (NH$_3$) (mole ratio EDA:MEA:NH$_3$ was 2.5:1:8.5) was passed over a phosphoric acid catalyst on a silica support at a gas hourly space velocity of 2500 vol/hr/vol based on all components, at 250 psig and 250° C. The resultant liquid product was distilled to remove two cuts: a TETA cut (140°–155° C. at 10 mm Hg) and a TEPA cut (190°–205° C. at 10 Hg mm). Analysis of the TETA cut is listed in Table V.

TABLE V

| TETA FEED COMPOSITION | |
|---|---|
| Component | TETA wt % |
| Diethylenetriamine (DETA) | 0.05 |
| Aminoethylethanolamine (AEEA) | 0.26 |
| Aminoethylpiperazine (AEP) | 0.00 |
| Tris(aminoethyl)amine (TAEA) | 10.06 |
| Triethylenetetramine (TETA) | 58.09 |
| Bis(aminoethyl)piperazine (BAEP) | 15.57 |
| Piperazinoethylethylenediamine (PEEDA) | 10.24 |

TABLE V-continued

| TETA FEED COMPOSITION | |
|---|---|
| Component | TETA wt % |
| Total Unknowns | 5.72 |
| Total Noncyclic Polyamines (TNC) | 68.2 |

Hydrogenation Decolorization: In this series of examples, a portion of the TETA cut (75 g) was charged to a 300 ml stainless steel autoclave which was equipped with a sintered metal filter capable of retaining all of the catalyst when the product was removed from the reactor. For Example 9, the hydrogenation catalyst (see Table VI) was added, and the autoclave was thoroughly flushed with hydrogen to remove adventitious air. After pressurization with hydrogen, the reaction mixture was heated with stirring (see Table VI for pressure, temperature and batch time). At the completion of the reaction cycle, the hydrogenated polyamines were removed from the reactor with the filter; the catalyst was retained in the reactor. Once the hydrogenated TETA product was removed from the reactor, the next batch was charged to the reactor and the cycle started again. The hydrogenated polyamines product was then distilled, and following these distillations, the product was analyzed. For each distillation, approximately 98% of the material was recovered leaving a small residue on the bottom of the distillation vessel. Feed, product (hydrogenation) and distillate color numbers are listed in Table VI. The product composition was then determined by GLC; product analyses are listed in Table VII.

would account for the ability to further reduce the color level by distillation. The logical conclusion of this theory is that it is these polymerized chromophores which are the residue formed during the distillation.

EXAMPLES 14–16

Effect of Changing Feed Composition

To determine the effect of different TETA compositions on the process of the present invention and the interaction between a particular composition and the operating conditions of the hydrogenation process, Examples 14–16 were run. It should be noted that variations in the compositions of either TETA or TEPA arise not only from changes in the process variables, e.g. feed ratio, gas hourly space velocity, temperature, etc., used during polyamine production, but also from fractionation of the product during distillation. Thus although identical process conditions may have been used to make several samples of crude polyamines with similar overall compositions, compositions of TETA and TEPA removed at differing times during distillation may vary markedly.

EXAMPLE 14

Preparation of TETA feed: A polyethylene poly-

TABLE VI

| | Catalyst, Operating Conditions, Feed Color and Product Color | | | | | | |
|---|---|---|---|---|---|---|---|
| Example | Catalyst (wt %) | Time (hr) | Temperature (° C.) | H$_2$ Pressure (psig) | Color Feed | Color Product | Dist |
| 9 | 5% Pd/C (4.1) | 4 | 100 | 400 | 7+ | 2 | 0 |
| 10 | 5% Pd/C (4.1) | 4 | 100 | 400 | 7+ | 4+ | 0 |
| 11 | 5% Pd/C (4.1) | 4 | 100 | 400 | 7+ | 4+ | 0 |
| 12 | 5% Pd/C (4.1) | 4 | 100 | 400 | 7+ | 5+ | 0 |
| 13 | 5% Pd/C (4.1) | 4 | 100 | 400 | 7+ | 6 | <1 |

TABLE VII

| EXAMPLE 9-13 PRODUCT COMPOSITIONS | | | | | | |
|---|---|---|---|---|---|---|
| Component | TETA wt % | EX 9 wt % | EX 10 wt % | EX 11 wt % | EX 12 wt % | EX 13 wt % |
| Diethylenetriamine (DETA) | 0.05 | 0.25 | 0.34 | 0.28 | 0.30 | 0.34 |
| Aminoethylethanolamine (AEEA) | 0.26 | >0.26 | 0.29 | 0.28 | 0.29 | 0.31 |
| Aminoethylpiperazine (AEP) | 0.00 | 0.36 | 0.29 | 0.24 | 0.22 | 0.22 |
| Tris(aminoethyl)amine (TAEA) | 10.06 | 9.59 | 9.85 | 9.92 | 9.83 | 9.82 |
| Triethylenetetramine (TETA) | 58.09 | 56.78 | 57.06 | 57.71 | 57.03 | 57.14 |
| Bis(aminoethyl)piperazine (BAEP) | 15.57 | 18.75 | 17.66 | 17.34 | 17.41 | 16.80 |
| Piperazinoethylethylenediamine (PEEDA) | 10.24 | 13.36 | 13.58 | 13.51 | 13.48 | 13.00 |
| Total Unknowns | 5.72 | 0.65 | 0.92 | 0.72 | 1.43 | 2.36 |
| Total Noncyclic Polyamines (TNC) | 68.2 | 66.6 | 67.25 | 67.9 | 67.2 | 67.3 |

As can be seen from the data for Examples 9-13, catalyst aging seems to reduce the effectiveness of direct decolorization of TETA fractions. Although not intending to be bound by the following theory, it is possible that as the catalyst ages the decolorization mechanism changes from directly reducing the number of chromophores in the product to polymerizing these chromophores into heavier molecules. This theory amine product was produced using the process of U.S. Pat. No. 4,503,253. A mixture of monoethanolamine (MEA), ethylenediamine (EDA) and ammonia (NH$_3$) (mole ratio EDA:MEA:NH$_3$ was 3:1:8.5) was passed over a phosphoric acid catalyst on a silica support at a gas hourly space velocity of 2500 vol/hr/vol based on all components, at 250 psig and 250° C. The resultant liquid product was distilled to remove two cuts: a TETA cut (140°-155° C. at 10 mm Hg) and a TEPA cut (190°-205° C. at 10 mm Hg). Analysis of the TETA cut is listed in Table VIII.

TABLE VIII

TETA FEED COMPOSITION

| Component | TETA wt % |
|---|---|
| Diethylenetriamine (DETA) | 0.04 |
| Aminoethylethanolamine (AEEA) | 0.22 |
| Aminoethylpiperazine (AEP) | 0.00 |
| Tris(aminoethyl)amine (TAEA) | 10.03 |
| Triethylenetetramine (TETA) | 67.06 |
| Bis(aminoethyl)piperazine (BAEP) | 18.82 |
| Piperazinoethylethylenediamine (PEEDA) | 1.17 |
| Total Unknowns | 2.65 |
| Total Noncyclic Polyamines (TNC) | 77.1 |

Hydrogenation Decolorization: The TETA cut (75 g), which is a mixture of isomers and had a color of 7 on the Gardner scale, was charged to a 300 ml stainless steel autoclave. 4.0 wt % of a 5% Pd/C hydrogenation catalyst was added, and the autoclave thoroughly flushed with hydrogen to remove adventitious air. After pressurization with hydrogen to 400 psig $H_2$, the reaction mixture was heated to 100° C. with stirring and held there for a period of 4 hours. At the completion of this reaction cycle, the hydrogenated polyamines were removed from the reactor and filtered to remove any retained catalyst. The filtered hydrogenated polyamine product had a color of <1. The product composition of the polyamine product is given in Table IX.

TABLE IX

TETA PRODUCT COMPOSITION

| Component | EX 14 wt % |
|---|---|
| Diethylenetriamine (DETA) | 0.18 |
| Aminoethylethanolamine (AEEA) | 0.23 |
| Aminoethylpiperazine (AEP) | 0.30 |
| Tris(aminoethyl)amine (TAEA) | 9.76 |
| Triethylenetetramine (TETA) | 66.72 |
| Bis(aminoethyl)piperazine (BAEP) | 19.43 |
| Piperazinoethylethylenediamine (PEEDA) | 2.17 |
| Total Unknowns | 1.21 |
| Total Noncyclic Polyamines (TNC) | 76.7 |

EXAMPLE 15

Preparation of TETA feed: A polyethylene polyamine product was produced using the process of U.S. Pat. No. 4,503,253. A mixture of monoethanolamine (MEA), ethylenediamine (EDA) and ammonia ($NH_3$) (mole ratio EDA:MEA:$NH_3$ was 2.5:1:8.5) was passed over a phosphoric acid catalyst on a silica support at a gas hourly space velocity of 2500 vol/hr/vol based on all components, at 250 psig and 250° C. The resultant liquid product was distilled to remove two cuts: a TETA cut (140°-155° C. at 10 mm Hg) and a TEPA cut (190°-205° C. at 10 mm Hg). Analysis of the TETA cut is listed in Table X.

TABLE X

TETA FEED COMPOSITION

| Component | TETA wt % |
|---|---|
| Diethylenetriamine (DETA) | 0.71 |
| Aminoethylethanolamine (AEEA) | 0.49 |
| Aminoethylpiperazine (AEP) | 0.33 |
| Tris(aminoethyl)amine (TAEA) | 11.90 |

TABLE X-continued

TETA FEED COMPOSITION

| Component | TETA wt % |
|---|---|
| Triethylenetetramine (TETA) | 50.57 |
| Bis(aminoethyl)piperazine (BAEP) | 27.83 |
| Piperazinoethylethylenediamine (PEEDA) | 5.00 |
| Total Unknowns | 3.17 |
| Total Noncyclic Polyamines (TNC) | 63.2 |

Hydrogenation Decolorization: The TETA cut (75 g), which is a mixture of isomers and had a color of 7 on the Gardner scale, was charged to a 300 ml stainless steel autoclave. 4.0 wt % of a 5% Pd/C hydrogenation catalyst was added, and the autoclave thoroughly flushed with hydrogen to remove adventitious air. After pressurization with hydrogen to 100 psig $H_2$, the reaction mixture was heated to 125° C. with stirring and held there for a period of 4 hours. At the completion of this reaction cycle, the hydrogenated polyamines were removed from the reactor and filtered to remove any retained catalyst. The filtered hydrogenated polyamine product had a color of 2+. The polyamine product was then distilled, like before, a small residue was left on the surface of the boiling flask and the polyamine product's color was reduced to 0. The product composition of the polyamine product is given in Table XI.

TABLE XI

TETA PRODUCT COMPOSITION

| Component | EX 15 wt % |
|---|---|
| Diethylenetriamine (DETA) | 0.89 |
| Aminoethylethanolamine (AEEA) | 0.48 |
| Aminoethylpiperazine (AEP) | 0.87 |
| Tris(aminoethyl)amine (TAEA) | 11.46 |
| Triethylenetetramine (TETA) | 48.86 |
| Bis(aminoethyl)piperazine (BAEP) | 28.04 |
| Piperazinoethylethylenediamine (PEEDA) | 5.46 |
| Total Unknowns | 3.93 |
| Total Noncyclic Polyamines (TNC) | 61.2 |

From this example, it appears that, like with catalyst aging, too low of a hydrogen partial pressure for a particular TETA composition also changes the color reduction mechanism from direct reduction of chromophores to polymerization of these chromophores into heavier molecules that can be removed by distillation. It is hypothesized that too low of hydrogen partial pressure will increase catalyst aging.

EXAMPLE 16

Preparation of TETA feed: A polyethylene polyamine product was produced using the process of U.S. Pat. No. 4,503,253. A mixture of monoethanolamine (MEA), ethylenediamine (EDA) and ammonia ($NH_3$) (mole ratio EDA:MEA:$NH_3$ was 2.5:1:8.5) was passed over a phosphoric acid catalyst on a silica support at a gas hourly space velocity of 2500 vol/hr/vol based on all components, at 250 psig and 250° C. The resultant liquid product was distilled to remove two cuts: a TETA cut (140°-155° C. at 10 mm Hg) and a TEPA cut (190°-205° C. at 10 mm Hg). Analysis of the TETA cut is listed in Table XII.

TABLE XII

TETA FEED COMPOSITION

| Component | TETA wt % |
|---|---|
| Diethylenetriamine (DETA) | 0.05 |
| Aminoethylethanolamine (AEEA) | 0.34 |
| Aminoethylpiperazine (AEP) | 0.32 |
| Tris(aminoethyl)amine (TAEA) | 12.18 |
| Triethylenetetramine (TETA) | 59.08 |
| Bis(aminoethyl)piperazine (BAEP) | 15.67 |
| Piperazinoethylethylenediamine (PEEDA) | 7.81 |
| Total Unknowns | 4.55 |
| Total Noncyclic Polyamines (TNC) | 71.3 |

Hydrogenation Decolorization: The TETA cut (75 g), which is a mixture of isomers and had a color of 7 on the Gardner scale, was charged to a 300 ml stainless steel autoclave. 2.0 wt % of a 5% Pd/C hydrogenation catalyst was added, and the autoclave thoroughly flushed with hydrogen to remove adventitious air. After pressurization with hydrogen to 75 psig $H_2$, the reaction mixture was heated to 100° C. with stirring and held there for a period of 4 hours. At the completion of this reaction cycle, the hydrogenated polyamines were removed from the reactor and filtered to remove any retained catalyst. The filtered hydrogenated polyamine product had a color of 1. The product composition of the polyamine product is given in Table XIII.

TABLE XIII

TETA PRODUCT COMPOSITION

| Component | EX 16 wt % |
|---|---|
| Diethylenetriamine (DETA) | 0.18 |
| Aminoethylethanolamine (AEEA) | 0.62 |
| Aminoethylpiperazine (AEP) | 0.38 |
| Tris(aminoethyl)amine (TAEA) | 12.36 |
| Triethylenetetramine (TETA) | 56.96 |
| Bis(aminoethyl)piperazine (BAEP) | 18.12 |
| Piperazinoethylethylenediamine (PEEDA) | 10.39 |
| Total Unknowns | 0.99 |
| Total Noncyclic Polyamines (TNC) | 69.5 |

EXAMPLES 17–19

Effect of Operating Conditions for TEPA Hydrotreating

To determine the effect of catalyst levels and operating conditions on the hydrogenation (decolorization) of TEPA the following examples were run.

Preparation of TEPA feed: A polyethylene polyamine product was produced using the process of U.S. Pat. No. 4,503,253. A mixture of monoethanolamine (MEA), ethylenediamine (EDA) and ammonia ($NH_3$) (mole ratio EDA:MEA:$NH_3$ was 2.5:1:8.5) was passed over a phosphoric acid catalyst on a silica support at a gas hourly space velocity of 2500 vol/hr/vol based on all components, at 250 psig and 250° C. The resultant liquid product was distilled to remove two cuts: a TETA cut (140°–155° C. at 10 mm Hg) and a TEPA cut (190°–205° C. at 10 mm Hg). Analysis of the TEPA cut is listed in Table XIV.

TABLE XIV

TEPA FEED COMPOSITION

| Component | TEPA wt % |
|---|---|
| Diethylenetriamine (DETA) | 0.00 |
| Aminoethylethanolamine (AEEA) | 0.03 |
| Aminoethylpiperazine (AEP) | 0.00 |
| Tris(aminoethyl)amine (TAEA) | 0.09 |
| Triethylenetetramine (TETA) | 0.61 |
| Bis(aminoethyl)piperazine (BAEP) | 0.16 |
| Piperazinoethylethylenediamine (PEEDA) | 0.28 |
| Aminoethyltriethylenetetraamine (AETETA) | 42.64 |
| Tetraethylenepentamine (TEPA) | 31.85 |
| Aminoethylbis(aminoethyl)piperazine (AEBAEP) | 16.46 |
| Aminoethyl(piperazinoethyl)ethylenediamine (AEPEEDA) | 0.22 |
| Total Unknowns | 6.74 |

Hydrogenation Decolorization: The TEPA cut (75 g) was charged to a 300 ml stainless steel autoclave. The hydrogenation catalyst (see Table XV) was added, and the autoclave was thoroughly flushed with hydrogen to remove adventitious air. After pressurization with hydrogen, the reaction mixture was heated with stirring (see Table XV for pressure, temperature and batch time). At the completion of the reaction cycle, the hydrogenated polyamines were removed from the reactor and filtered to remove any retained catalyst. The product was then distilled to further remove any color bodies which has polymerized during the hydrogenation. Feed, product and distillate color numbers are listed in Table XV.

TABLE XV

Catalyst, Operating Conditions, Feed Color and Product Color

| Example | Catalyst (wt %) | Time (hr) | Temperature (° C.) | $H_2$ Pressure (psig) | Color Feed | Color Product | Dist |
|---|---|---|---|---|---|---|---|
| 17 | 5% Pd/C (4.0) | 4 | 100 | 400 | 9 | 5+ | 4 |
| 18 | 5% Pd/C (2.5) | 1 | 125 | 400 | 9 | 6+ | 5 |
| 19 | 5% Pd/C (4.0) | 1 | 125 | 75 | 9 | 8+ | 6 |

The product composition was then determined by GLC; product analyses are listed in Table III.

TABLE XIII

TEPA PRODUCT COMPOSITION

| Component | EX 17 wt % | EX 18 wt % | EX 19 wt % |
|---|---|---|---|
| Diethylenetriamine (DETA) | 0.06 | 0.14 | 0.21 |
| Aminoethylethanolamine (AEEA) | 0.13 | 0.05 | 0.06 |
| Aminoethylpiperazine (AEP) | 0.07 | 0.12 | 0.15 |
| Tris(aminoethyl)amine (TAEA) | 0.45 | 0.26 | 0.34 |
| Triethylenetetramine (TETA) | 0.30 | 0.27 | 0.35 |
| Bis(aminoethyl)piperazine (BAEP) | 0.75 | 0.41 | 0.27 |
| Piperazinoethylethylenediamine (PEEDA) | 0.70 | 0.68 | 0.65 |
| Aminoethyltriethylenetetraamine (Aeteta) | 40.41 | 35.52 | 42.03 |
| Tetraethylenepentamine (TEPA) | 30.39 | 31.79 | 30.10 |
| Aminoethylbis(aminoethyl)piperazine (AEBAEP) | 17.39 | 22.22 | 17.20 |
| Aminoethyl(piperazinoethyl)ethylenediamine (AEPEEDA) | 0.58 | 1.11 | 0.64 |
| Total Unknowns | 6.90 | 6.15 | 6.97 |

EXAMPLE 20

Effect of a Crude Polyamine Feed

To determine whether mixtures of polyethylene amines could be decolorized by the method of the present invention, a mixed polyamines product was produced by using the process of U.S. Pat. No. 4,503,253. A mixture of monoethanolamine (MEA), ethylenediamine (EDA) and ammonia ($NH_3$) (mole ratio EDA:MEA:$NH_3$ was 2.5:1:8.5) was passed over a phosphoric acid catalyst on a silica support at a gas hourly space velocity of 2500 vol/hr/vol based on all components, at 250 psig and 250° C. The resultant liquid product was distilled into a crude fraction consisting of 4% AEEA, 66% TETA and 30% TEPA. The crude fraction has a color of 11. This crude fraction was hydrotreated in an autoclave with a 5% Pd/C (4.1 wt%, dry basis, relative to total polyamines) at 100° C. and 400 psig for a period of two hours. The hydrogenation product was then filtered to remove any entrained catalyst; color for the filtrate was 7. The filtered product was then distilled to produce a TETA and TEPA cut. The TETA cut (95% recovery) had a color of 1 and the TEPA (90% recovery) had a color of 4. Owing to the stability of the individual polyamines under similar operating conditions, a product composition analysis was not performed.

EXAMPLE 21

Effect of Catalyst Drying

In all other examples in which 5% Pd/C was used as the hydrogenation catalyst, the stated catalyst incorporations were accompanied by an equal weight of water which was included in the catalyst during the manufacture. To determine the effect of removing this water, the following example was run.

Preparation of TETA feed: A polyethylene polyamine product was produced using the process of U.S. Pat. No. 4,503,253. A mixture of monoethanolamine (MEA), ethylenediamine (EDA) and ammonia ($NH_3$) (mole ratio EDA:MEA:$NH_3$ was 2.5:1:9) was passed over a phosphoric acid catalyst on a silica support at a gas hourly space velocity of 2500 vol/hr/vol based on all components, at 250 psig and 250° C. The resultant liquid product was distilled to remove two cuts: a TETA cut (140°–155° C. at 10 mm Hg) and a TEPA cut (190°–205° C. at 10 mm Hg). Analysis of the TETA cut is listed in Table XIV.

TABLE XIV

| TETA FEED COMPOSITION | |
|---|---|
| Component | TETA wt % |
| Diethylenetriamine (DETA) | 0.03 |
| Aminoethylethanolamine (AEEA) | 0.18 |
| Aminoethylpiperazine (AEP) | 0.00 |
| Tris(aminoethyl)amine (TAEA) | 11.72 |
| Triethylenetetramine (TETA) | 59.27 |
| Bis(aminoethyl)piperazine (BAEP) | 15.49 |
| Piperazinoethylethylenediamine (PEEDA) | 7.89 |
| Total Unknowns | 5.42 |
| Total Noncyclic Polyamines (TNC) | 71.0 |

Hydrogenation Decolorization: The TETA cut (60 g), which is a mixture of isomers and had a color of 11 on the Gardner scale, was charged to a 125 ml stainless steel autoclave. 5.2 wt % of a 5% Pd/C hydrogenation catalyst which had been dried at 70° C. at 50 mm Hg for 24 hours to a constant weight was added, and the autoclave thoroughly flushed with hydrogen to remove adventitious air. After pressurization with hydrogen to 500 psig $H_2$, the reaction mixture was heated to 125° C. with stirring and held there for a period of 18 hours. At the completion of this reaction cycle, the hydrogenated polyamines were removed from the reactor and filtered to remove any retained catalyst. The filtered hydrogenated polyamine product had a color of 0. The product composition of the polyamine product is given in Table XV.

TABLE XV

| TETA PRODUCT COMPOSITION | |
|---|---|
| Component | EX 15 wt % |
| Diethylenetriamine (DETA) | 0.39 |
| Aminoethylethanolamine (AEEA) | 0.19 |
| Aminoethylpiperazine (AEP) | 0.40 |
| Tris(aminoethyl)amine (TAEA) | 11.22 |
| Triethylenetetramine (TETA) | 56.91 |
| Bis(aminoethyl)piperazine (BAEP) | 17.87 |
| Piperazinoethylethylenediamine (PEEDA) | 12.26 |
| Total Unknowns | 0.76 |
| Total Noncyclic Polyamines (TNC) | 68.5 |

From this example, little difference was noted between the compositions of the TETA feed and product with the exception that the concentration of unknowns diminished, while the concentration of the cyclic TETA isomers increased.

Based on the foregoing examples, it is evident that the present invention is effective for the removal of color from polyamines. As demonstrated by the examples, the hydrogenation process can be carried out in a batch operation and, although not shown by example, it would follow that the process is also capable of being carried out in a continuous operation utilizing for example, a fixed bed packed reactor or a continuous stirred tank reactor (CSTR). Three hydrogenation catalysts have been demonstrated, Raney nickel, Pd/C and Ru/C. Nevertheless, it is logical to assume that any metallic hydrogenation catalysts which are effective for organic compounds would be usable in the process. Effective catalytic metals are nickel, palladium, ruthenium, molybdenum, tungsten, cobalt and chromium. These catalytic metals can be supported on standard base materials, e.g. carbon, silica, alumina, aluminosilicates or used in an unsupported mode. As for operating conditions, these would be related to the chemical composition of the polyamine being hydrogenated and the catalyst used for the hydrogenation. In general, operating conditions would be in the following range:

Temperature: °C. 50 to 175
Pressure: psig 50 to 1500
Batch Times: hr 0.1 to 4
Space Velocity: v/hr/v 0.01 to 10

The present invention has been described with reference to several preferred embodiments thereof. However, these embodiments should not be considered a limitation on the scope of the invention, which scope should be ascertained by the following claims.

We claim:

1. A process for the reduction of color of a polyamine product which comprises contacting said polyamine at elevated temperature and pressure with a catalytically effective amount of a hydrogenation catalyst, selected from the group consisting of palladium on carbon, ruthenium on carbon and mixtures thereof, in the presence of a hydrogen-containing atmosphere.

2. The process of claim 1 wherein said elevated temperature is in the range of 50° to 175° C.

3. The process of claim 1 wherein said elevated pressure is in the range of 50 to 1500 psig.

4. The process of claim 1 wherein said elevated temperature is in the range of 50° to 175° C. and said elevated pressure is in the range of 50 to 1500 psig.

5. The process of claim 1 wherein said polyamine product is a triethylenetetramine cut.

6. The process of claim 1 wherein said polyamine product is a tetraethylenepentamine cut.

7. The process of claim 1 wherein said polyamine product is a crude polyamine product.

8. The process of claim 1 which further comprises distilling said polyamine following said contacting step to further reduce color.

9. In a process for producing polyethylene polyamines by reacting monoethanolamine and ethylenediamine in the presence of a catalytically effective amount of a phosphorous-containing catalyst, the improvement comprising contacting said polyamine at elevated temperature and pressure with a catalytically effective amount of a hydrogenation catalyst, selected from the group consisting of palladium on carbon, ruthenium on carbon and mixtures thereof, in the presence of a hydrogen-containing atmosphere.

10. The process of claim 9 wherein the reaction of monoethanolamine and ethylenediamine is carried out in the vapor phase.

* * * * *